(12) United States Patent
Beck et al.

(10) Patent No.: US 7,763,004 B2
(45) Date of Patent: Jul. 27, 2010

(54) DISPOSABLE ABSORBENT ARTICLE HAVING LAYERED CONTAINMENT POCKETS

(75) Inventors: Theodora Beck, Colerain Township, OH (US); Gary Dean LaVon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 468 days.

(21) Appl. No.: 11/131,799

(22) Filed: May 18, 2005

(65) Prior Publication Data

US 2006/0264860 A1 Nov. 23, 2006

(51) Int. Cl.
*A61F 13/15* (2006.01)

(52) U.S. Cl. .......... 604/385.28; 604/358; 604/385.01; 604/385.04; 604/385.101; 604/385.201; 604/385.21; 604/385.23; 604/385.24; 604/385.25; 604/385.26; 604/385.27

(58) Field of Classification Search ............ 604/385.28, 604/358, 385.01, 385.04, 385.101, 385.201, 604/385.21, 385.23, 385.24, 385.25, 385.26, 604/385.27
See application file for complete search history.

(56) References Cited

U.S. PATENT DOCUMENTS

| | | | |
|---|---|---|---|
| 1,364,663 A | 1/1921 | Walker |
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjombak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |

(Continued)

FOREIGN PATENT DOCUMENTS

DE 19732499 2/1999

(Continued)

OTHER PUBLICATIONS

International Search Report.

(Continued)

*Primary Examiner*—Tatyana Zalukaeva
*Assistant Examiner*—Ginger T Chapman
(74) *Attorney, Agent, or Firm*—Richard L. Alexander

(57) ABSTRACT

A disposable absorbent article including a chassis and an absorbent assembly. The chassis is folded laterally inward and outward in a zigzag pattern to form laterally opposing layered containment pockets and laterally opposing side flaps interiorly of the layered containment pockets. Each side flap has a longitudinally extending elastic gathering member attached adjacent to its distal edge. The absorbent assembly includes an absorbent core that may contain superabsorbent particles, which may be contained inside pockets.

11 Claims, 8 Drawing Sheets

U.S. PATENT DOCUMENTS

| | | | |
|---|---|---|---|
| 2,931,361 A | 4/1960 | Sostsrin | |
| 2,977,957 A | 4/1961 | Clyne | |
| 3,180,335 A * | 4/1965 | Baker et al. | 604/375 |
| 3,207,158 A | 9/1965 | Yoshitake et al. | |
| 3,386,442 A | 6/1968 | Sabee | |
| 3,561,446 A | 2/1971 | Jones | |
| 3,572,342 A | 3/1971 | Lindquist et al. | |
| 3,572,432 A | 3/1971 | Burton | |
| 3,578,155 A | 5/1971 | Small et al. | |
| 3,592,194 A | 7/1971 | Duncan | |
| 3,610,244 A | 10/1971 | Jones | |
| 3,618,608 A | 11/1971 | Brink | |
| 3,642,001 A | 2/1972 | Sabee | |
| 3,653,381 A | 4/1972 | Warnken | |
| 3,688,767 A | 9/1972 | Goldstein | |
| 3,710,797 A | 1/1973 | Marsan | |
| 3,731,688 A * | 5/1973 | Litt et al. | 604/365 |
| 3,756,878 A | 9/1973 | Willot | |
| 3,774,241 A | 11/1973 | Zerkle | |
| 3,776,233 A | 12/1973 | Schaar | |
| 3,814,100 A | 6/1974 | Nystrand et al. | |
| 3,828,784 A | 8/1974 | Zoephel | |
| 3,840,418 A | 10/1974 | Sabee | |
| 3,847,702 A | 11/1974 | Jones | |
| 3,848,595 A | 11/1974 | Endres | |
| 3,848,597 A | 11/1974 | Endres | |
| 3,860,003 A | 1/1975 | Buell | |
| 3,863,637 A | 2/1975 | MacDonald et al. | |
| 3,882,870 A | 5/1975 | Hathaway | |
| 3,884,234 A | 5/1975 | Taylor | |
| 3,900,032 A | 8/1975 | Heurlen | |
| 3,920,017 A | 11/1975 | Karami | |
| 3,924,626 A * | 12/1975 | Lee et al. | 604/366 |
| 3,926,189 A | 12/1975 | Taylor | |
| 3,929,134 A | 12/1975 | Karami | |
| 3,929,135 A | 12/1975 | Thompson | |
| 3,930,501 A | 1/1976 | Schaar | |
| 3,938,523 A | 2/1976 | Gilliland et al. | |
| 3,968,799 A | 7/1976 | Schrading | |
| 3,978,861 A | 9/1976 | Schaar | |
| 3,981,306 A | 9/1976 | Krusko | |
| 3,987,794 A | 10/1976 | Schaar | |
| 3,995,637 A | 12/1976 | Schaar | |
| 3,995,640 A | 12/1976 | Schaar | |
| 3,999,547 A | 12/1976 | Hernandez | |
| 4,014,338 A | 3/1977 | Schaar | |
| 4,034,760 A | 7/1977 | Amirsakis | |
| 4,074,508 A | 2/1978 | Reid | |
| 4,084,592 A | 4/1978 | Tritsch | |
| 4,100,922 A | 7/1978 | Hernandez | |
| 4,257,418 A | 3/1981 | Hessner | |
| 4,296,750 A | 10/1981 | Woon et al. | |
| 4,315,508 A | 2/1982 | Bolick | |
| 4,324,246 A | 4/1982 | Mullane et al. | |
| 4,342,314 A | 8/1982 | Radel et al. | |
| 4,388,075 A | 6/1983 | Mesek et al. | |
| 4,461,621 A | 7/1984 | Karami et al. | |
| 4,463,045 A | 7/1984 | Ahr et al. | |
| 4,475,912 A | 10/1984 | Coates | |
| 4,490,148 A | 12/1984 | Beckeström | |
| 4,578,072 A | 3/1986 | Lancaster | |
| 4,578,702 A | 3/1986 | Campbell | |
| 4,585,450 A | 4/1986 | Rosch et al. | |
| 4,589,878 A | 5/1986 | Mitrani | |
| 4,601,717 A | 7/1986 | Blevins | |
| 4,610,678 A | 9/1986 | Weisman et al. | |
| 4,623,342 A | 11/1986 | Ito et al. | |
| 4,636,207 A | 1/1987 | Buell | |
| 4,670,011 A | 6/1987 | Mesek | |
| 4,670,012 A | 6/1987 | Johnson | |
| 4,680,030 A | 7/1987 | Coates et al. | |
| 4,681,579 A | 7/1987 | Toussant et al. | |
| 4,681,581 A | 7/1987 | Coates | |
| 4,690,680 A | 9/1987 | Higgins | |
| 4,695,278 A | 9/1987 | Lawson | |
| 4,704,115 A | 11/1987 | Buell | |
| 4,704,116 A | 11/1987 | Enloe | |
| 4,731,066 A | 3/1988 | Korpman | |
| 4,731,070 A * | 3/1988 | Koci | 604/385.201 |
| 4,747,846 A | 5/1988 | Boland et al. | |
| 4,781,711 A * | 11/1988 | Houghton et al. | 604/378 |
| 4,787,896 A * | 11/1988 | Houghton et al. | 604/385.23 |
| 4,788,722 A | 12/1988 | Oliver | |
| 4,795,454 A | 1/1989 | Dragoo | |
| 4,802,884 A | 2/1989 | Fröidh et al. | |
| 4,808,176 A | 2/1989 | Kielpikowski | |
| 4,834,735 A | 5/1989 | Alemany et al. | |
| 4,834,740 A | 5/1989 | Suzuki et al. | |
| 4,834,742 A | 5/1989 | Wilson et al. | |
| 4,838,886 A | 6/1989 | Kent | |
| 4,846,825 A | 7/1989 | Enloe et al. | |
| 4,861,652 A | 8/1989 | Lippert et al. | |
| 4,888,231 A | 12/1989 | Angstadt | |
| 4,892,528 A | 1/1990 | Suzuki et al. | |
| 4,892,536 A | 1/1990 | DesMarais et al. | |
| 4,900,317 A | 2/1990 | Buell | |
| 4,904,251 A | 2/1990 | Igaue et al. | |
| 4,909,802 A | 3/1990 | Ahr et al. | |
| 4,909,803 A | 3/1990 | Aziz et al. | |
| 4,938,753 A | 7/1990 | Van Gompel et al. | |
| 4,940,463 A | 7/1990 | Leathers et al. | |
| 4,940,464 A | 7/1990 | Van Gompel et al. | |
| 4,950,264 A | 8/1990 | Osborn | |
| 4,963,140 A | 10/1990 | Robertson et al. | |
| 4,968,313 A | 11/1990 | Sabee | |
| 4,990,147 A | 2/1991 | Freeland | |
| 5,006,394 A | 4/1991 | Baird | |
| 5,032,120 A | 7/1991 | Freeland et al. | |
| 5,037,416 A | 8/1991 | Allen et al. | |
| 5,071,414 A | 12/1991 | Elliott | |
| 5,085,654 A | 2/1992 | Buell | |
| 5,092,861 A | 3/1992 | Nomura et al. | |
| 5,114,420 A | 5/1992 | Igaue et al. | |
| 5,135,522 A | 8/1992 | Fahrenkrug et al. | |
| D329,697 S | 9/1992 | Fahrenkrug et al. | |
| 5,151,092 A | 9/1992 | Buell et al. | |
| 5,190,606 A | 3/1993 | Merkatoris et al. | |
| 5,204,997 A | 4/1993 | Suzuki et al. | |
| 5,221,274 A | 6/1993 | Buell et al. | |
| 5,235,515 A | 8/1993 | Ungpiyakul et al. | |
| 5,246,431 A | 9/1993 | Minetola et al. | |
| 5,246,432 A | 9/1993 | Suzuki et al. | |
| 5,246,433 A | 9/1993 | Hasse et al. | |
| 5,260,345 A | 11/1993 | Desmarais et al. | |
| 5,269,775 A | 12/1993 | Freeland et al. | |
| 5,312,386 A | 5/1994 | Correa et al. | |
| 5,358,500 A | 10/1994 | LaVon et al. | |
| 5,366,782 A | 11/1994 | Curro et al. | |
| 5,368,585 A | 11/1994 | Dokken | |
| 5,387,209 A | 2/1995 | Yamamoto et al. | |
| 5,397,316 A | 3/1995 | LaVon et al. | |
| H1440 H | 5/1995 | New et al. | |
| 5,415,644 A | 5/1995 | Enloe | |
| 5,476,458 A | 12/1995 | Glaug et al. | |
| 5,507,895 A | 4/1996 | Suekane | |
| 5,518,801 A * | 5/1996 | Chappell et al. | 428/152 |
| 5,531,730 A | 7/1996 | Dreier | |
| 5,542,943 A | 8/1996 | Sageser | |
| 5,549,592 A | 8/1996 | Fries et al. | |
| 5,549,593 A | 8/1996 | Ygge et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |

| | | | | | | |
|---|---|---|---|---|---|---|
| 5,584,829 A | 12/1996 | Lavash et al. | | 6,306,121 B1 | 10/2001 | Damaghi et al. |
| 5,607,416 A | 3/1997 | Yamamoto et al. | | 6,306,122 B1 | 10/2001 | Narawa et al. |
| 5,607,537 A | 3/1997 | Johnson et al. | | 6,322,552 B1 | 11/2001 | Blenke et al. |
| 5,607,760 A | 3/1997 | Roe | | 6,325,787 B1 | 12/2001 | Roe et al. |
| 5,609,587 A | 3/1997 | Roe | | 6,334,858 B1 | 1/2002 | Rönnberg et al. |
| 5,622,589 A | 4/1997 | Johnson et al. | | 6,350,332 B1 | 2/2002 | Thomas et al. |
| 5,624,424 A | 4/1997 | Saisaka et al. | | 6,402,729 B1 | 6/2002 | Boberg et al. |
| 5,625,222 A | 4/1997 | Yoneda et al. | | 6,402,731 B1 | 6/2002 | Suprise et al. |
| 5,626,571 A | 5/1997 | Young et al. | | 6,410,820 B1 | 6/2002 | McFall et al. |
| 5,635,191 A | 6/1997 | Roe et al. | | 6,413,249 B1 | 7/2002 | Turi et al. |
| 5,643,243 A | 7/1997 | Klemp | | 6,419,667 B1 | 7/2002 | Avalon et al. |
| 5,643,588 A | 7/1997 | Roe et al. | | 6,423,048 B1 | 7/2002 | Suzuki et al. |
| 5,649,920 A | 7/1997 | LaVon et al. | | 6,432,098 B1 | 8/2002 | Kline et al. |
| H1674 H | 8/1997 | Ames et al. | | 6,432,099 B2 | 8/2002 | Rönnberg |
| 5,662,638 A | 9/1997 | Johnson et al. | | 6,440,117 B1 | 8/2002 | Itoh et al. |
| 5,669,901 A | 9/1997 | LaFortune et al. | | 6,443,933 B1 | 9/2002 | Suzuki et al. |
| 5,674,215 A | 10/1997 | Ronnberg | | 6,461,342 B2 | 10/2002 | Tanji et al. |
| 5,685,874 A | 11/1997 | Buell et al. | | 6,461,343 B1 | 10/2002 | Schaefer et al. |
| 5,691,035 A | 11/1997 | Chappell et al. | | 6,475,201 B2 | 11/2002 | Saito et al. |
| 5,695,488 A | 12/1997 | Sosalla | | 6,478,786 B1 | 11/2002 | Glaug et al. |
| 5,723,087 A | 3/1998 | Chappell et al. | | 6,494,872 B1 | 12/2002 | Suzuki et al. |
| 5,733,275 A | 3/1998 | Davis et al. | | 6,494,873 B2 | 12/2002 | Karlsson et al. |
| 5,749,866 A | 5/1998 | Roe et al. | | 6,520,947 B1 | 2/2003 | Tilly et al. |
| 5,752,947 A * | 5/1998 | Awolin .................. 604/387 | | 6,524,294 B1 | 2/2003 | Hilston et al. |
| 5,769,838 A | 6/1998 | Buell et al. | | 6,547,774 B2 | 4/2003 | Ono et al. |
| 5,772,825 A | 6/1998 | Schmitz | | 6,585,712 B2 | 7/2003 | Yoshimasa |
| 5,776,121 A | 7/1998 | Roe et al. | | 6,585,713 B1 | 7/2003 | LeMahieu et al. |
| 5,779,831 A | 7/1998 | Schmitz | | 6,602,234 B2 | 8/2003 | Klemp et al. |
| 5,797,894 A | 8/1998 | Cadieux et al. | | 6,605,070 B2 | 8/2003 | Ludwig et al. |
| 5,810,800 A | 9/1998 | Hunter et al. | | 6,626,881 B2 | 9/2003 | Shingu et al. |
| 5,814,035 A | 9/1998 | Gryskiewicz et al. | | 6,648,869 B1 | 11/2003 | Gillies et al. |
| 5,820,618 A | 10/1998 | Roberts et al. | | 6,648,870 B2 | 11/2003 | Itoh et al. |
| 5,836,932 A | 11/1998 | Buell et al. | | 6,648,871 B2 | 11/2003 | Kusibojoska et al. |
| 5,846,232 A | 12/1998 | Serbiak et al. | | 6,652,696 B2 | 11/2003 | Kuen et al. |
| 5,851,204 A | 12/1998 | Mitzutani | | 6,682,515 B1 | 1/2004 | Mizutani et al. |
| 5,853,402 A | 12/1998 | Faulks et al. | | 6,682,596 B2 | 1/2004 | Zehnder et al. |
| 5,858,013 A | 1/1999 | Kling | | 6,689,115 B1 | 2/2004 | Popp et al. |
| 5,865,823 A | 2/1999 | Curro | | 6,726,792 B1 | 4/2004 | Johnson et al. |
| 5,873,868 A | 2/1999 | Nakahata | | 6,730,070 B2 | 5/2004 | Holmquist |
| 5,876,391 A | 3/1999 | Roe et al. | | 6,755,808 B2 | 6/2004 | Balogh et al. |
| 5,891,544 A | 4/1999 | Chappell et al. | | 6,761,711 B1 | 7/2004 | Fletcher et al. |
| 5,897,545 A | 4/1999 | Kline et al. | | 6,793,649 B1 | 9/2004 | Fujioka et al. |
| 5,904,673 A | 5/1999 | Roe et al. | | 6,818,083 B2 | 11/2004 | McAmish et al. |
| 5,931,825 A | 8/1999 | Kuen et al. | | 6,840,930 B2 | 1/2005 | Miyamoto et al. |
| 5,947,949 A | 9/1999 | Inoue et al. | | 6,849,067 B2 | 2/2005 | Fletcher et al. |
| 5,951,536 A | 9/1999 | Osborn, III et al. | | 6,880,211 B2 | 4/2005 | Jackson et al. |
| 5,957,908 A | 9/1999 | Kline et al. | | 6,923,797 B2 | 8/2005 | Shinohara et al. |
| 5,968,029 A | 10/1999 | Chappell et al. | | 6,962,578 B1 | 11/2005 | LaVon |
| 5,997,521 A | 12/1999 | Robles et al. | | 6,972,010 B2 | 12/2005 | Pesce et al. |
| 6,004,306 A | 12/1999 | Robles et al. | | 7,013,941 B2 | 3/2006 | Schneider et al. |
| 6,022,430 A | 2/2000 | Blenke et al. | | 7,014,632 B2 | 3/2006 | Takino et al. |
| 6,022,431 A | 2/2000 | Blenke et al. | | 7,014,649 B2 | 3/2006 | Bacher |
| 6,042,673 A | 3/2000 | Johnson et al. | | 7,037,299 B2 | 5/2006 | Turi et al. |
| 6,102,892 A | 8/2000 | Putzer et al. | | 7,048,726 B2 | 5/2006 | Kusagawa et al. |
| 6,107,537 A | 8/2000 | Elder et al. | | 7,066,921 B2 | 6/2006 | Schmoker et al. |
| 6,110,157 A | 8/2000 | Schmidt | | 7,094,227 B2 | 8/2006 | Ishiguro et al. |
| 6,117,121 A | 9/2000 | Faulks et al. | | 7,112,193 B2 | 9/2006 | Otsubo |
| 6,117,803 A | 9/2000 | Morman et al. | | 7,195,622 B2 | 3/2007 | Lindstrom |
| 6,120,486 A | 9/2000 | Toyoda et al. | | 7,288,079 B2 | 10/2007 | Toyoshima et al. |
| 6,120,487 A | 9/2000 | Ashton | | 7,291,137 B2 | 11/2007 | LaVon et al. |
| 6,120,489 A | 9/2000 | Johnson et al. | | 7,320,684 B2 | 1/2008 | LaVon et al. |
| 6,120,866 A | 9/2000 | Arakawa et al. | | 7,347,848 B2 | 3/2008 | Fernfors |
| 6,129,720 A | 10/2000 | Blenke et al. | | 7,435,243 B2 | 10/2008 | Miyamoto et al. |
| 6,156,424 A | 12/2000 | Taylor | | 7,435,244 B2 | 10/2008 | Schroer, Jr. et al. |
| 6,165,160 A | 12/2000 | Suzuki et al. | | 7,458,960 B2 | 12/2008 | Otsubo et al. |
| 6,174,302 B1 | 1/2001 | Kumasaka | | 7,462,172 B2 | 12/2008 | Wright et al. |
| 6,177,607 B1 | 1/2001 | Blaney et al. | | 2001/0021834 A1 * | 9/2001 | Yoshimasa ............. 604/385.01 |
| 6,186,996 B1 | 2/2001 | Martin | | 2002/0045881 A1 | 4/2002 | Kusibojoska et al. |
| 6,210,386 B1 | 4/2001 | Inoue | | 2002/0087139 A1 | 7/2002 | Popp et al. |
| 6,210,390 B1 | 4/2001 | Karlsson | | 2002/0151858 A1 | 10/2002 | Karami et al. |
| 6,238,380 B1 | 5/2001 | Sasaki | | 2002/0173764 A1 * | 11/2002 | Takino et al. .......... 604/385.28 |
| 6,241,716 B1 | 6/2001 | Rönnberg | | 2002/0173767 A1 | 11/2002 | Popp et al. |
| 6,258,077 B1 | 7/2001 | Buell et al. | | 2003/0003269 A1 | 1/2003 | Lee et al. |

| | | | |
|---|---|---|---|
| 2003/0023220 A1 | 1/2003 | Ukegawa et al. | |
| 2003/0088223 A1 | 5/2003 | Vogt et al. | |
| 2003/0105447 A1 | 6/2003 | Widlund et al. | |
| 2003/0144644 A1 | 7/2003 | Murai et al. | |
| 2003/0148694 A1 | 8/2003 | Ghiam | |
| 2003/0233082 A1 | 12/2003 | Kline et al. | |
| 2004/0022998 A1 | 2/2004 | Miyamoto et al. | |
| 2004/0064126 A1 | 4/2004 | Fletcher et al. | |
| 2004/0082928 A1 | 4/2004 | Pesce et al. | |
| 2004/0082932 A1 | 4/2004 | Lauritzen | |
| 2004/0103234 A1 | 5/2004 | Zer et al. | |
| 2004/0122404 A1 | 6/2004 | Meyer et al. | |
| 2004/0122411 A1 | 6/2004 | Hancock-Cooke | |
| 2004/0127868 A1 | 7/2004 | Olson et al. | |
| 2004/0147890 A1 | 7/2004 | Nakahata et al. | |
| 2004/0162536 A1 | 8/2004 | Becker et al. | |
| 2004/0167486 A1 | 8/2004 | Busam et al. | |
| 2004/0193133 A1 | 9/2004 | Desai et al. | |
| 2004/0225271 A1 | 11/2004 | Datta et al. | |
| 2004/0236299 A1 | 11/2004 | Tsang et al. | |
| 2004/0249355 A1 | 12/2004 | Tanio et al. | |
| 2005/0004548 A1 | 1/2005 | Otsubo et al. | |
| 2005/0038401 A1 | 2/2005 | Suzuki et al. | |
| 2005/0085784 A1 | 4/2005 | LeMinh et al. | |
| 2005/0119634 A1 | 6/2005 | Fletcher et al. | |
| 2005/0171499 A1* | 8/2005 | Nigam et al. | 604/385.22 |
| 2005/0203475 A1 | 9/2005 | LaVon et al. | |
| 2005/0288645 A1 | 12/2005 | LaVon | |
| 2005/0288646 A1 | 12/2005 | LaVon | |
| 2006/0264860 A1 | 11/2006 | Beck | |
| 2006/0264861 A1 | 11/2006 | LaVon et al. | |
| 2006/0271010 A1 | 11/2006 | LaVon | |
| 2006/0293637 A1 | 12/2006 | LaVon et al. | |
| 2007/0032770 A1 | 2/2007 | LaVon et al. | |
| 2007/0049897 A1 | 3/2007 | LaVon et al. | |
| 2007/0066951 A1 | 3/2007 | LaVon et al. | |
| 2007/0066952 A1 | 3/2007 | LaVon et al. | |
| 2007/0066953 A1 | 3/2007 | LaVon et al. | |
| 2007/0118088 A1 | 5/2007 | LaVon | |
| 2007/0173780 A1 | 5/2007 | LaVon et al. | |
| 2007/0173782 A1 | 7/2007 | LaVon | |
| 2008/0033389 A1 | 2/2008 | Bandorf et al. | |
| 2008/0077115 A1 | 3/2008 | Reyes | |
| 2008/0183149 A1 | 7/2008 | LaVon et al. | |
| 2008/0208155 A1 | 7/2008 | LaVon et al. | |
| 2008/0208156 A1 | 8/2008 | LaVon et al. | |
| 2008/0234649 A1 | 9/2008 | Hamall et al. | |

FOREIGN PATENT DOCUMENTS

| | | | |
|---|---|---|---|
| EP | 0 206 208 A1 | 12/1986 | |
| EP | 374542 | 6/1990 | |
| EP | 0 403 832 B1 | 12/1990 | |
| EP | 0 761 194 A2 | 3/1997 | |
| EP | 0 893 115 A2 | 1/1999 | |
| EP | 0 916 327 B1 | 5/1999 | |
| EP | 0 951 890 A2 | 10/1999 | |
| EP | 0 793 469 B9 | 6/2002 | |
| EP | 1 224 922 A2 | 7/2002 | |
| EP | 1 447 066 A1 | 8/2004 | |
| EP | 1 447 067 A1 | 8/2004 | |
| ES | 2 213 491 A1 | 8/2004 | |
| FR | 2 566 631 A1 | 1/1986 | |
| FR | 2 612 770 A1 | 9/1988 | |
| FR | 2 810 234 A1 | 12/2001 | |
| GB | 1 307 441 | 2/1973 | |
| GB | 1 513 055 | 6/1978 | |
| GB | 2 101 468 A | 1/1983 | |
| GB | 2 262 873 A | 7/1993 | |
| JP | 04 122256 A | 4/1992 | |
| JP | 11318980 | 11/1999 | |
| WO | WO 95/16746 | 6/1995 | |
| WO | WO 95/19753 | 7/1995 | |
| WO | WO 95/29657 A1 | 11/1995 | |
| WO | WO 98/16179 A1 | 4/1998 | |
| WO | WO 99/13813 | 3/1999 | |
| WO | WO 99/13813 A1 | 3/1999 | |
| WO | WO 03/009794 A3 | 2/2003 | |
| WO | WO 2004/105664 | 12/2004 | |
| WO | WO 05/016211 | 2/2005 | |
| WO | WO 05/074851 | 8/2005 | |
| WO | WO 05/081937 | 9/2005 | |
| WO | WO 2005/087164 A1 | 9/2005 | |
| WO | WO 06/074481 | 7/2006 | |
| WO | WO 2007/000315 A1 | 1/2007 | |

OTHER PUBLICATIONS

International Search Report, 2006.
U.S. Appl. No. 10/880,128, filed Jun. 29, 2004, Office Action dated Dec. 18, 2009.
U.S. Appl. No. 10/880,128, filed Jun. 29, 2004, Office Action dated Jun. 30, 2009.
U.S. Appl. No. 10/880,128, filed Jun. 29, 2004, Office Action dated Dec. 4, 2008.
U.S. Appl. No. 10/880,128, filed Jun. 29, 2004, Office Action dated Jun. 12, 2008.
U.S. Appl. No. 10/880,128, filed Jun. 29, 2004, Office Action dated Dec. 10, 2007.
U.S. Appl. No. 10/880,128, filed Jun. 29, 2004, Office Action dated Jun. 22, 2007.
U.S. Appl. No. 10/880,128, filed Jun. 29, 2004, Office Action dated Jan. 26, 2007.
U.S. Appl. No. 11/133,818, filed May 20, 2005, Office Action dated Nov. 9, 2009.
U.S. Appl. No. 11/133,818, filed May 20, 2005, Office Action dated Apr. 1, 2009.
U.S. Appl. No. 11/133,818, filed May 20, 2005, Office Action dated Dec. 9, 2008.
U.S. Appl. No. 11/133,818, filed May 20, 2005, Office Action dated Jun. 18, 2008.
U.S. Appl. No. 11/133,818, filed May 20, 2005, Office Action dated Dec. 31, 2007.
U.S. Appl. No. 11/133,818, filed May 20, 2005, Office Action dated Jun. 26, 2007.
U.S. Appl. No. 11/159,916, filed Jun. 23, 2005, Patent Issuance dated Nov. 17, 2009.
U.S. Appl. No. 11/159,916, filed Jun. 23, 2005, Office Action dated Sep. 17, 2009.
U.S. Appl. No. 11/159,916, filed Jun. 23, 2005, Office Action dated Mar. 6, 2009.
U.S. Appl. No. 11/159,916, filed Jun. 23, 2005, Office Action dated Apr. 18, 2008.
U.S. Appl. No. 11/159,916, filed Jun. 23, 2005, Office Action dated Nov. 1, 2007.
U.S. Appl. No. 11/231,511, filed Sep. 12, 2005, Office Action dated Sep. 28, 2009.
U.S. Appl. No. 11/231,511, filed Sep. 12, 2005, Office Action dated Jun. 19, 2009.
U.S. Appl. No. 11/231,511, filed Sep. 12, 2005, Office Action dated Dec. 30, 2008.
U.S. Appl. No. 11/231,511, filed Sep. 12, 2005, Office Action dated Sep. 23, 2008.
U.S. Appl. No. 11/231,511, filed Sep. 12, 2005, Office Action dated Mar. 4, 2008.
U.S. Appl. No. 11/231,511, filed Sep. 12, 2005, Office Action dated Jun. 7, 2006.
U.S. Appl. No. 11/231,511, filed Sep. 12, 2005, Office Action dated Jun. 7, 2006.
U.S. Appl. No. 11/231,512, filed Sep. 12, 2005, Office Action dated Jul. 22, 2009.
U.S. Appl. No. 11/231,512, filed Sep. 12, 2005, Office Action dated Jan. 6, 2009.
U.S. Appl. No. 11/231,512, filed Sep. 12, 2005, Office Action dated Jun. 27, 2008.

U.S. Appl. No. 11/231,500, filed Sep. 21, 2005, Office Action dated Sep. 28, 2009.
U.S. Appl. No. 11/231,500, filed Sep. 21, 2005, Office Action dated Jun. 24, 2009.
U.S. Appl. No. 11/231,500, filed Sep. 21, 2005, Office Action dated Jan. 8, 2009.
U.S. Appl. No. 11/231,500, filed Sep. 21, 2005, Office Action dated Sep. 22, 2008.
U.S. Appl. No. 11/231,500, filed Sep. 21, 2005, Office Action dated Mar. 4, 2008.
U.S. Appl. No. 11/231,500, filed Sep. 21, 2005, Office Action dated Aug. 22, 2007.
U.S. Appl. No. 11/231,500, filed Sep. 21, 2005, Office Action dated Jun. 8, 2006.
U.S. Appl. No. 11/232,193, filed Sep. 21, 2005, Patent Issuance dated Jan. 22, 2008.
U.S. Appl. No. 11/232,193, filed Sep. 21, 2005, Office Action dated Aug. 28, 2007.
U.S. Appl. No. 11/232,193, filed Sep. 21, 2005, Office Action dated Jun. 7, 2006.
U.S. Appl. No. 11/286,612, filed Nov. 23, 2005, Office Action dated Jan. 4, 2010.
U.S. Appl. No. 11/286,612, filed Nov. 23, 2005, Office Action dated Jul. 23, 2009.
U.S. Appl. No. 11/286,612, filed Nov. 23, 2005, Office Action dated Dec. 24, 2008.

* cited by examiner

DISPOSABLE ABSORBENT ARTICLE HAVING LAYERED CONTAINMENT POCKETS

FIELD OF THE INVENTION

The invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

A simple disposable absorbent article includes a chassis and an absorbent assembly. Laterally opposing side portions of the chassis are folded in a zigzag pattern to form laterally opposing layered containment pockets serving to receive and contain bodily waste and thereby prevent this waste from migrating laterally and escaping. The distal closed apex of each containment pocket is formed at a longitudinally extending line along which the chassis is folded laterally inward. The upper edge of the proximal open side of each containment pocket is defined by another longitudinally extending line along which the chassis is folded laterally outward. The zigs and zags forming the layered containment pockets may be attached together in an overlapping arrangement. Above each uppermost layered containment pocket, the remainder of the respective side portion of the chassis is folded laterally outward to form a side flap. Each side flap preferably includes a longitudinally extensible flap elastic member that is attached adjacent to the distal edge of the side flap. The chassis may include an extensible formed web material.

The absorbent assembly includes an absorbent core. The absorbent core may contain superabsorbent particles and these particles may be contained inside pockets. Laterally opposing side portions of the absorbent assembly may be folded along with the respective side portions of the chassis to form one or more of the layered containment pockets and thereby provide absorbency in the pocket or pockets.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In FIG. 1, the interior portion of the diaper 20 that faces inwardly toward the wearer and contacts the wearer is shown facing the viewer.

In FIG. 7, the interior portion of the diaper 20 that faces inwardly toward the wearer and contacts the wearer is shown facing the viewer.

In FIG. 11, the absorbent assembly 200 is shown separately from a chassis 100 to which it is attached in an exemplary diaper 20 and the interior portion of the absorbent assembly 200 that faces inwardly toward the wearer and contacts the wearer is shown facing the viewer.

DETAILED DESCRIPTION OF THE INVENTION

Figure 1:
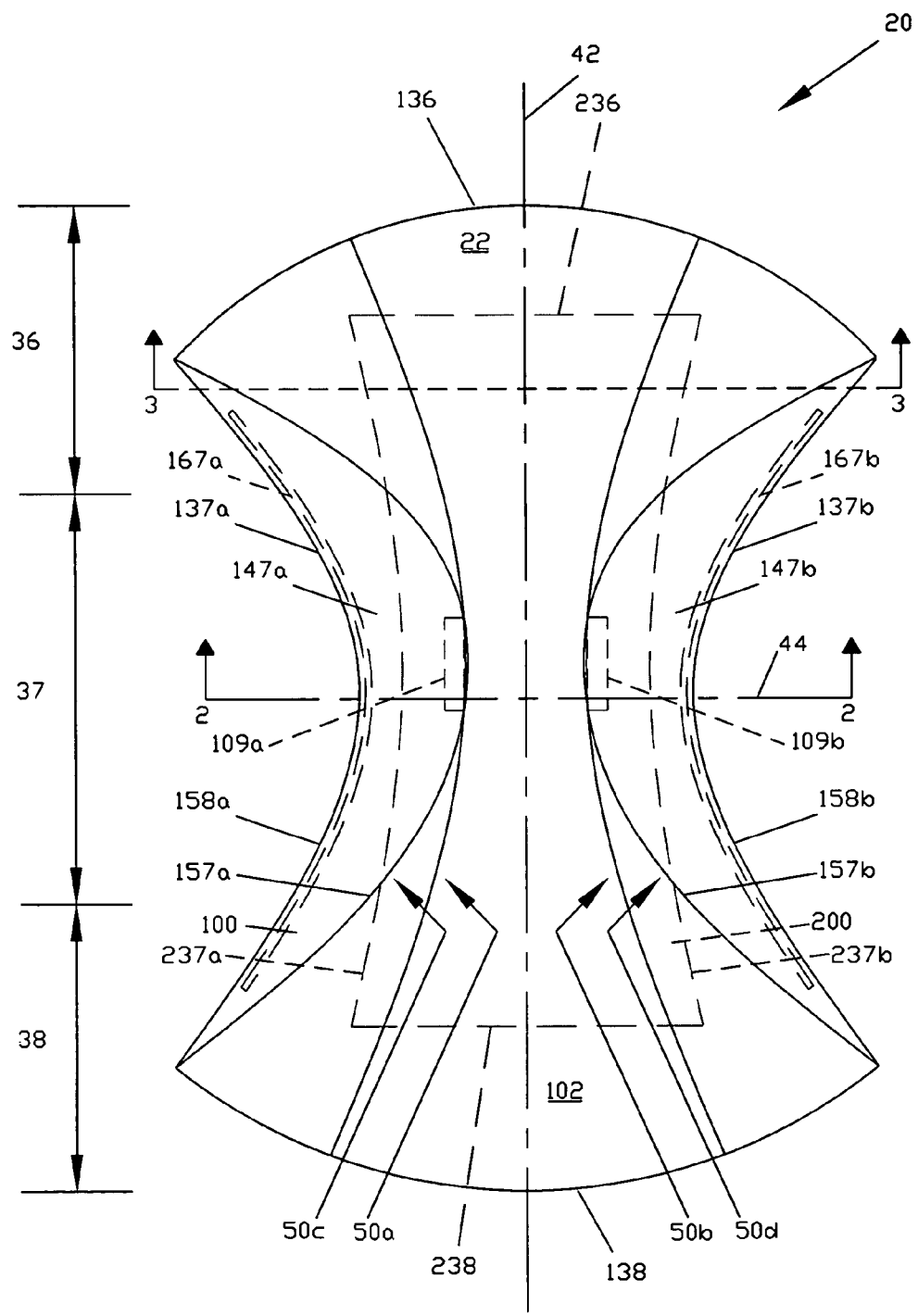
FIG. 1 is a plan view of an exemplary disposable absorbent article in the form of a diaper 20, which is shown in its flat, uncontracted state, i.e., without the contraction induced by elastic members.

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso so as to encircle the waist and the legs of a wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "longitudinal" refers to a direction running from a waist edge to an opposing waist edge of the article and generally parallel to the maximum linear dimension of the article. Directions within 45 degrees of the longitudinal direction are considered to be "longitudinal" The term "lateral" refers to a direction running from a side edge to an opposing side edge of the article and generally at a right angle to the longitudinal direction. Directions within 45 degrees of the lateral direction are considered to be "lateral".

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables and Nonwovens Association).

The terms "proximal" and "distal" refer respectively to the location of an element relatively near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

In the following description and in the drawing figures, various structural elements are identified by reference numerals without suffixed letters when referring to the group as a whole and by the same reference numerals with suffixed letters when distinguishing between, for example, left and right members of the group. As an example, the side flaps as a group are identified by the reference numeral 147 while the individual left and right side flaps are respectively designated as elements 147a and 147b.

Description of Exemplary Diaper Embodiment

Reference is made to FIG. 1, FIG. 2, FIG. 3, FIG. 4, FIG. 5, and FIG. 6 for this section of this description.

One end portion of the exemplary diaper 20 is configured as a front waist region 36. The longitudinally opposing end portion of the diaper 20 is configured as a back waist region 38. An intermediate portion of the diaper 20 extending longitudinally between the front waist region 36 and the back waist region 38 is configured as a crotch region 37.

The basic structure of the diaper 20 includes a chassis 100. The chassis 100 has a laterally extending front waist edge 136 in the front waist region 36 and a longitudinally opposing and laterally extending back waist edge 138 in the back waist region 38. The chassis 100 has a longitudinally extending left side edge 137a and a laterally opposing and longitudinally extending right side edge 137b, both chassis side edges extending longitudinally between the front waist edge 136 and the back waist edge 138. The chassis 100 has an interior surface 102 and an exterior surface 104. The chassis 100 also has a longitudinal axis 42 and a lateral axis 44. The longitudinal axis 42 extends through the midpoint of the front waist edge 136 and through the midpoint of the back waist edge 138 of the chassis 100. The lateral axis 44 extends through the midpoint of the left side edge 137a and through the midpoint of the right side edge 137b of the chassis 100. The chassis 100 has longitudinally extending and laterally opposing layered containment pockets 50 and longitudinally extending and laterally opposing side flaps 147 that are described in more detail below.

The basic structure of the diaper 20 also includes an absorbent assembly 200 that is attached to the chassis 100. The absorbent assembly 200 has a laterally extending front edge 236 in the front waist region 36 and a longitudinally opposing and laterally extending back edge 238 in the back waist region 38. The absorbent assembly 200 has a longitudinally extending left side edge 237a and a laterally opposing and longitudinally extending right side edge 237b, both absorbent assembly side edges extending longitudinally between the front edge 236 and the back edge 238. The absorbent assembly 200 has an interior surface 202 and an exterior surface 204. The absorbent assembly 200 may be disposed symmetrically with respect to either or both of the longitudinal axis 42 and the lateral axis 44. Alternatively, the absorbent assembly 200 may be disposed asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically with respect to the lateral axis 44. In particular, the absorbent assembly 200 shown in FIG. 1 is disposed asymmetrically toward the front waist region 36.

The respective front edge 236, back edge 238, left side edge 237a, and right side edge 237b of the absorbent assembly 200 may lie inward of the respective front waist edge 136, back waist edge 138, left side edge 137a, and right side edge 137b of the chassis 100, as in the exemplary diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers of the chassis adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 may coincide with the corresponding edge or edges of the chassis 100.

Figure 4:
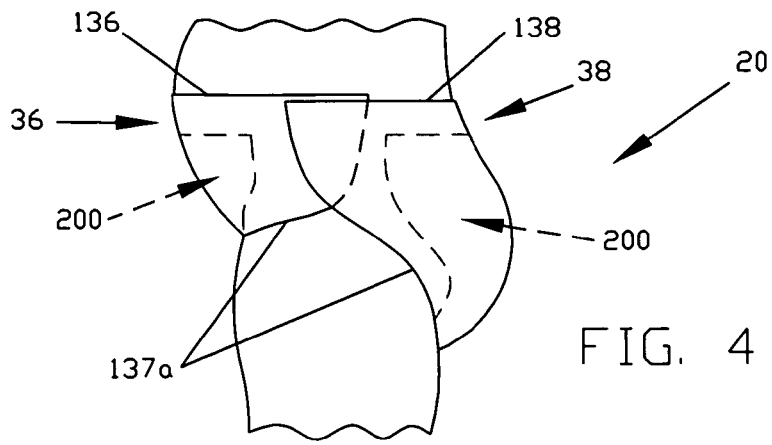
FIG. 4 is a simplified side elevation view of an exemplary diaper 20 being worn about a lower torso of a wearer.
Figure 5:
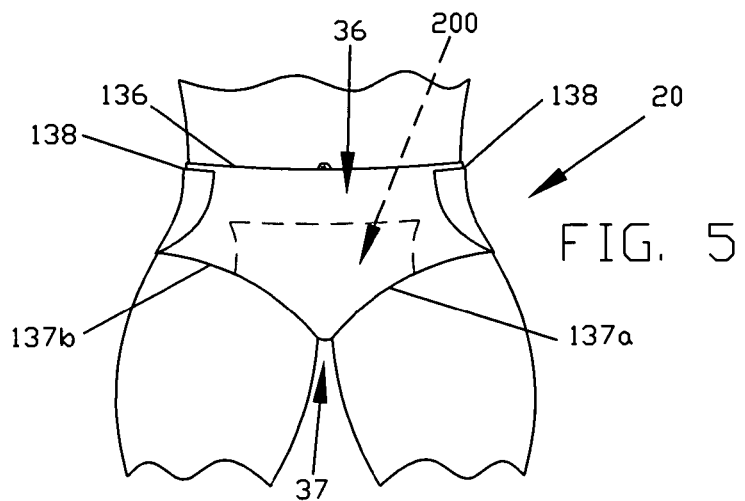
FIG. 5 is a front elevation view of the diaper 20 of FIG. 4 being worn about the lower torso of the wearer.
Figure 6:
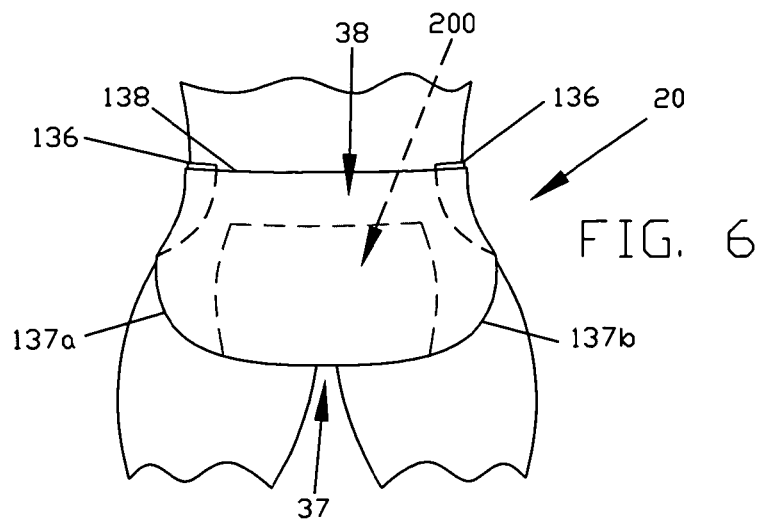
FIG. 6 is a back elevation view of the diaper 20 of FIG. 4 being worn about the lower torso of the wearer.

As shown in FIG. 4, FIG. 5, and FIG. 6, when the diaper 20 is worn on the lower torso of a wearer, the front waist edge 136 and the back waist edge 138 encircle the waist of the wearer, while at the same time the chassis side edges 137a and 137b encircle the legs of the wearer. At the same time, the crotch region 37 is generally positioned between the legs of the wearer and the absorbent assembly 200 extends from the front waist region 36 through the crotch region 37 to the back waist region 38.

Description of the Chassis

Figure 7:
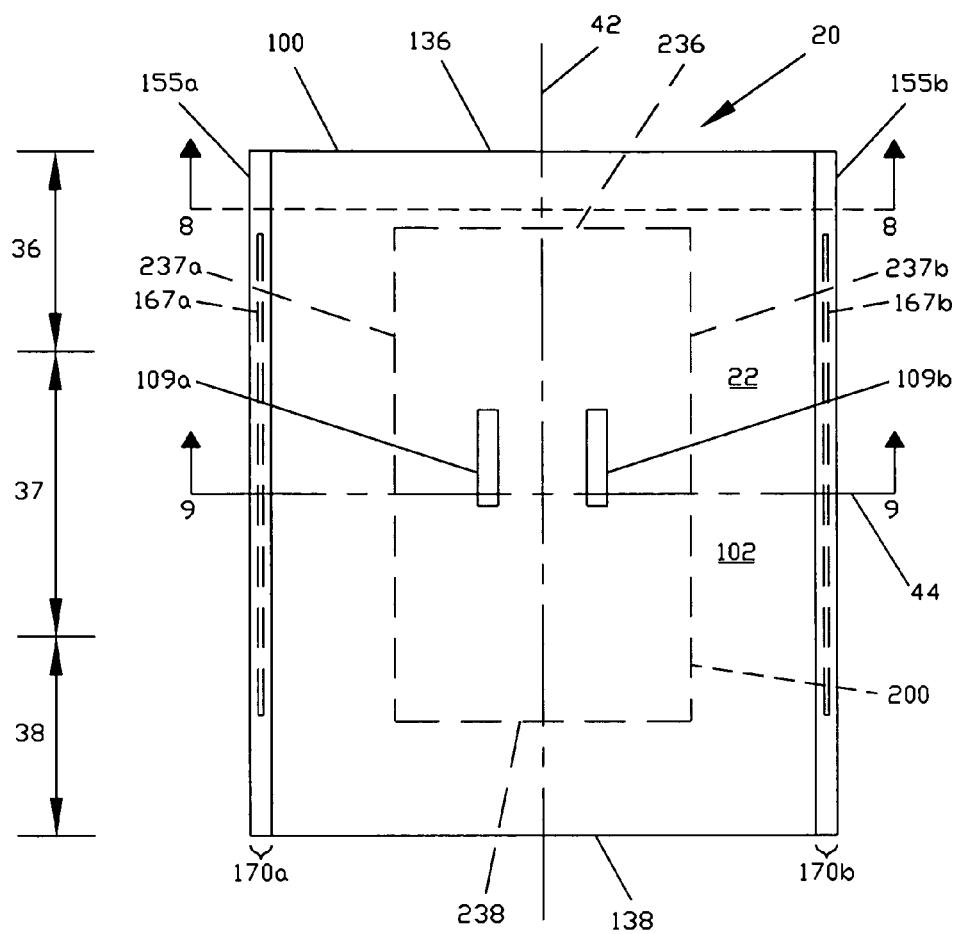
FIG. 7 is a plan view of an exemplary diaper 20 shown in its flat, uncontracted state, i.e., without the contraction induced by elastic members, before the containment pockets 50 and the side flaps 147a and 147b are formed by folding portions of the chassis 100.
Figure 8:
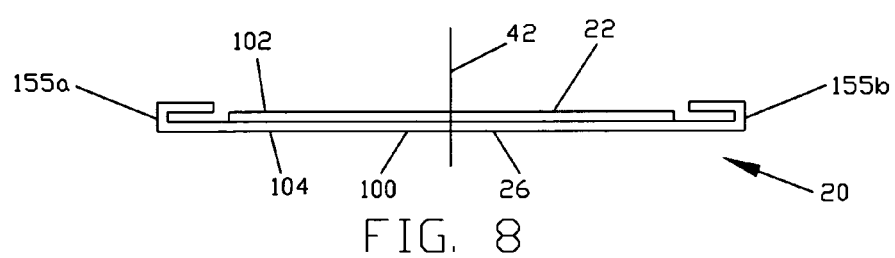
FIG. 8 is a section view of the diaper 20 of FIG. 7 taken at the section line 8-8.
Figure 9:
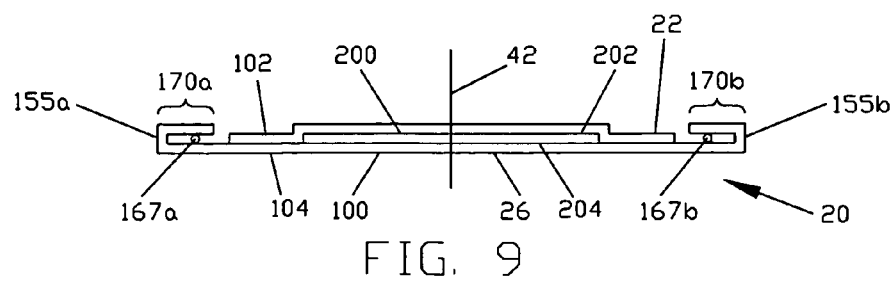
FIG. 9 is a section view of the diaper 20 of FIG. 7 taken at the section line 9-9, which coincides with the lateral axis 44 shown in FIG. 7.

In FIG. 7, FIG. 8, and FIG. 9, the exemplary chassis 100 is shown laid out flat before the containment pockets 50 and the side flaps 147 are formed by folding portions of the chassis. In this condition of being laid out flat, the chassis 100 has a longitudinally extending left outer side edge 155a and a laterally opposing and longitudinally extending right outer side edge 155b. Both of these chassis outer side edges extend longitudinally between the front waist edge 136 and the back waist edge 138. As is described in more detail below, when the side flaps 147 are formed by folding portions of the chassis 100 laterally outward, the outer side edges 155 of the chassis form the distal edges 158 of the side flaps.

The chassis 100 includes a water-impermeable backsheet 26. The backsheet 26 forms an exterior surface that is intended to be placed toward any clothing that is worn over the diaper 20. Many suitable materials for use as the backsheet 26 are well-known, including films of polyethylene and other polyolefins. Multi-layer backsheets, such as laminates of a film and a nonwoven, are also well-known and may be suitable for use as the backsheet 26. Such a laminate backsheet may be oriented with the nonwoven disposed exteriorly to provide the feel and appearance of a more cloth-like outermost layer than would be provided by using the film as the outermost layer.

The chassis 100 may, but need not, additionally include an inner liner 22 attached to the backsheet 26. The inner liner 22 may form a portion of the interior surface 102 of the chassis 100 that is intended to be placed against the body of the wearer. For example, the inner liner may cover and thereby lie interiorly of a portion or all of the absorbent assembly 200. The inner liner 22 preferably is formed of a soft material that will not irritate the skin of the wearer. Such an inner liner 22 may serve to isolate the skin of the wearer from a portion of the backsheet 26 as may be desirable, for example, when the diaper 20 is worn under conditions in which contact between the skin and a backsheet film could be uncomfortable. Many suitable materials for the inner liner 22 are well-known in the art, including rayon and synthetic nonwovens such as spunbonded or carded polypropylene or polyester.

The inner liner 22 may extend to the same width and the same length as the backsheet 26. Alternatively, one or more of the edges of the inner liner 22 may lie inward of the edges of the backsheet 26. For example, with reference to the exemplary diaper 20 shown in FIG. 1, only the portions of the backsheet 26 lying in the gaps between the front edge 236 of the absorbent assembly 200 and the front waist edge 136 of the chassis 100 and between the back edge 238 of the absorbent assembly 200 and the back waist edge 138 of the chassis 100 would need to be covered in order to isolate the skin of the wearer from the backsheet 26. Therefore, a laterally extending strip of the inner liner 22 disposed in the gap in the front waist region 36 and a similar laterally extending strip of the inner liner 22 disposed in the gap in the back waist region 38 may suffice.

Figure 2:
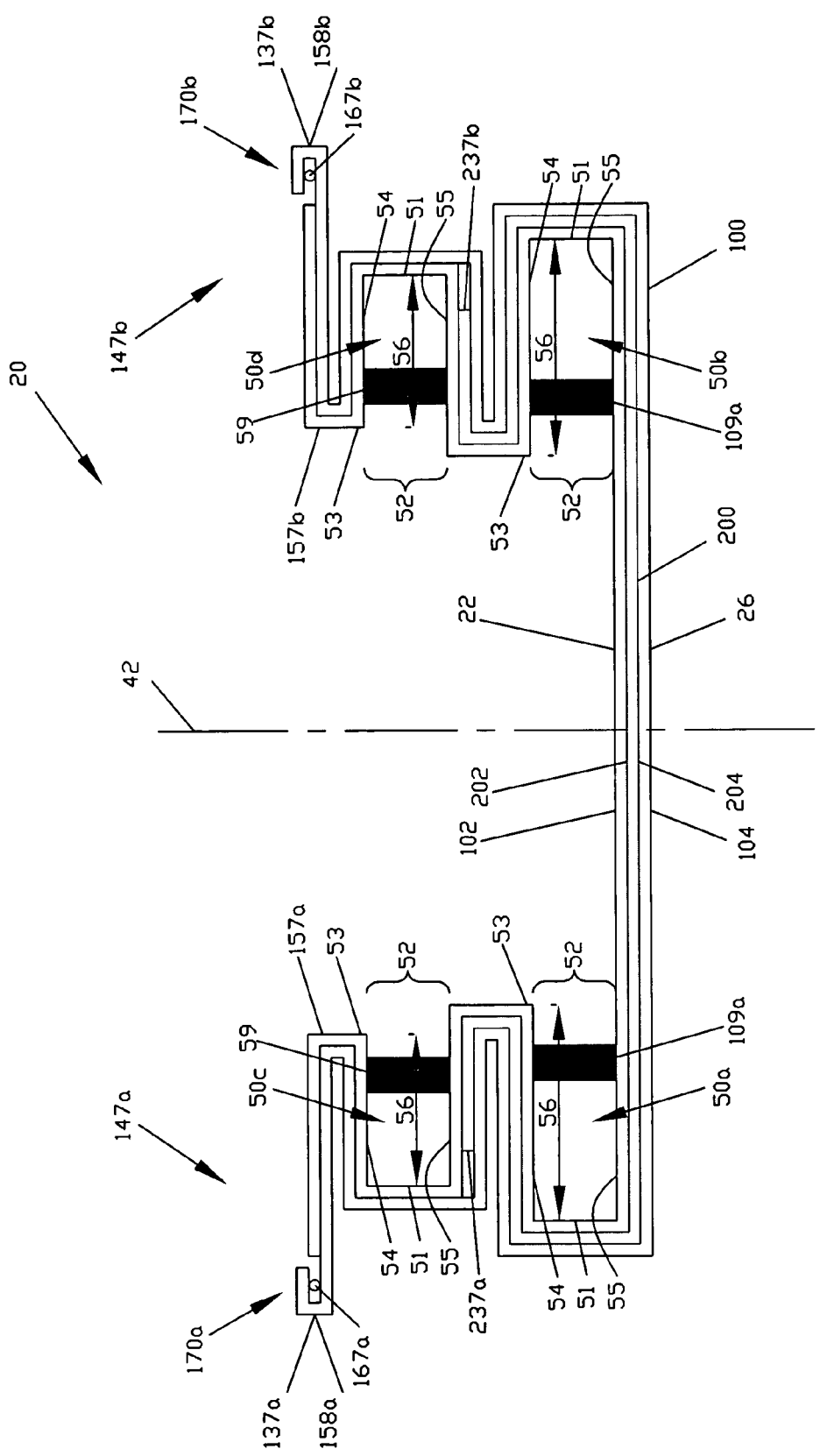
FIG. 2 is a section view of the diaper 20 of FIG. 1 taken at the section line 2-2, which coincides with the lateral axis 44 shown in FIG. 1.
Figure 3:
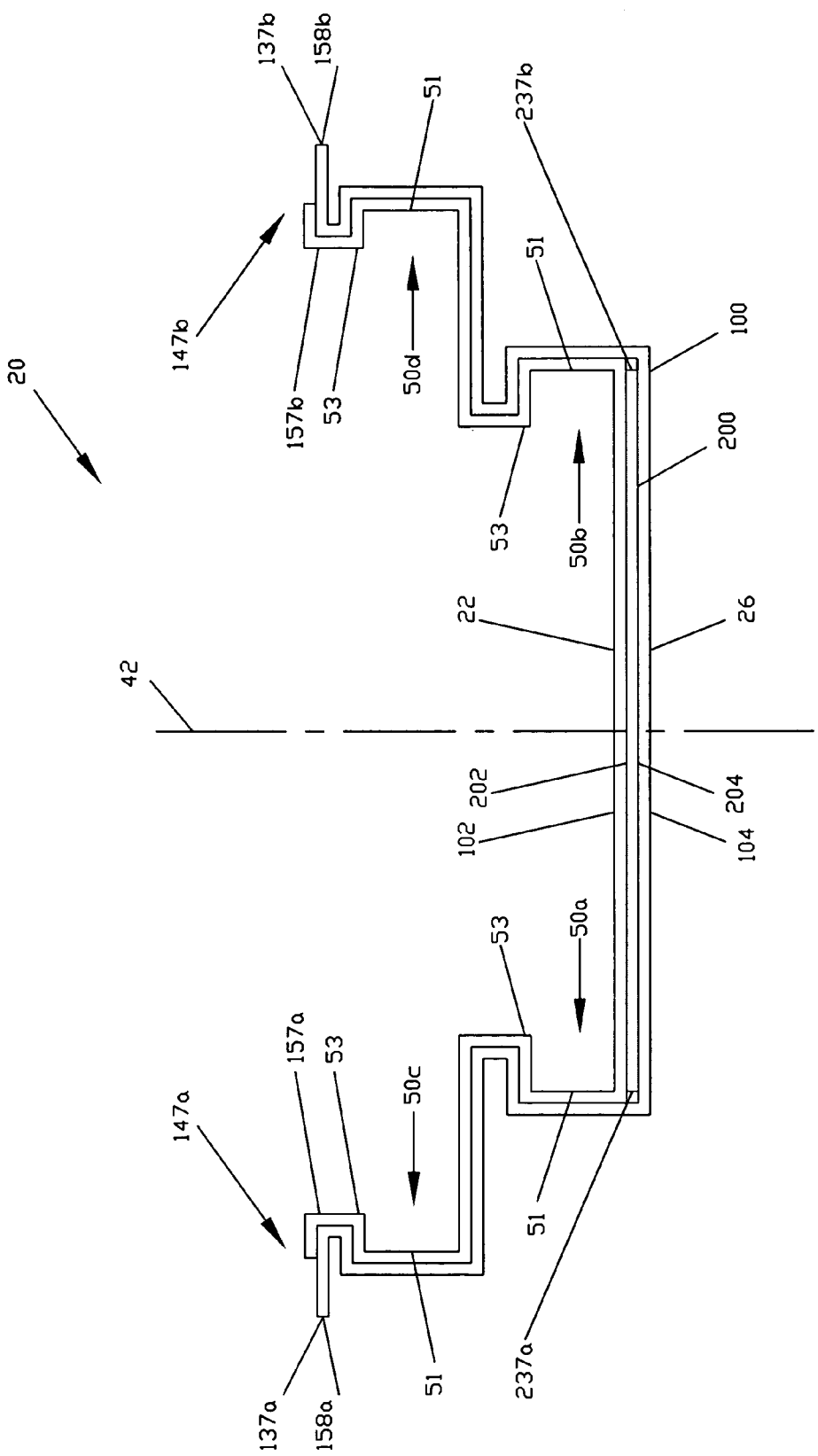
FIG. 3 is a section view of the diaper 20 of FIG. 1 taken at the section line 3-3 in the front waist region 36 shown in FIG. 1.

As shown in FIG. 1, FIG. 2, and FIG. 3, the exemplary chassis 100 has longitudinally extending and laterally opposing layered containment pockets 50 disposed in the crotch region 37 where they can serve to receive and contain bodily waste and thereby prevent this waste from migrating laterally and escaping from the disposable diaper. Each containment pocket has a closed apex 51 where a portion of the chassis is folded laterally inward, i.e., toward the longitudinal axis 42, and has an open side 52 having an upper edge 53 where a portion of the chassis is folded laterally outward, i.e., away from the longitudinal axis. Thus, with reference to the lateral direction, the apex of each containment pocket is disposed relatively distally and the upper edge of the open side of the same containment pocket is disposed relatively proximally, such that the open side of each containment pocket is proximally located, i.e., the pocket opens toward the longitudinal axis. Each containment pocket also has an upper wall 54 and a lower wall 55, each extending laterally inward from the apex 51, and each upper wall 54 connecting the apex 51 and the upper edge 53.

The lowermost laterally opposing containment pockets 50a and 50b are formed by the first laterally inward folds forming their apices 51 and laterally outward folds forming their upper edges 53. Each overlying containment pocket is formed by a similar zigzag pattern of folds forming its apex 51 and its upper edge 53. For example, in FIG. 1 and FIG. 2, two layered containment pockets are shown on each side of the longitudinal axis 42, namely lowermost containment pockets 50a and 50b and respective overlying containment pockets 50c and 50d. By repeating the zigzag pattern of folds, third containment pockets can be layered, fourth containment pockets can be layered, and so on.

The respective upper edges 53 of the layered containment pockets 50 may be superposed where they intersect the lateral axis 44, i.e., lie at substantially the same lateral distance from the longitudinal axis 42 and thus be laterally equidistantly disposed. Alternatively, the respective upper edges may be staggered, i.e., the distances from the upper edges to the longitudinal axis may be different, such that the upper edges of any of the overlying containment pockets may be disposed either laterally distally or laterally proximally relative to the upper edges of the lowermost containment pockets. For example, in FIG. 2, the upper edges 53 of the overlying containment pockets 50c and 50d are disposed laterally distally relative to the upper edges 53 of the lowermost containment pockets 50a and 50b.

The respective distal apices 51 of the layered containment pockets may similarly be superposed, i.e., lie at substantially the same lateral distance from the longitudinal axis 42, or may be staggered. For example, in FIG. 2, the apices 51 of the overlying containment pockets 50c and 50d are disposed laterally proximally relative to the apices 51 of the lowermost containment pockets 50a and 50b.

Furthermore, the respective depths of the layered containment pockets, as defined by their respective upper edges and their respective distal apices, may be substantially the same or alternatively their depths may be different. For example, in FIG. 2, the upper edges 53 and the apices 51 of the overlying containment pockets 50c and 50d are relatively closer together than the upper edges 53 and the apices 51 of the lowermost containment pockets 50a and 50b and thus the depths 56 of the overlying containment pockets 50c and 50d are relatively smaller than the depths 56 of the lowermost containment pockets 50a and 50b.

The folds forming the apices and the upper edges of the layered containment pockets may simply be folded loosely or may be creased. For example, it may be desirable to crease portions of the folds particularly in the crotch region in order to impart a more finished appearance to the diaper.

In the crotch region 37, the upper walls 54 of the lowermost containment pockets 50a and 50b may be attached to the interior surface 102 of the chassis 100, or to the interior surface 202 of the absorbent assembly 200 if the absorbent assembly is not covered by a layer of the chassis, in such a way as to prevent their unfoldment when lateral tension is applied. Any overlying containment pocket 50 whose proximal upper edge 53 lies laterally proximally relative to the proximal upper edge of the lowermost containment pocket may similarly be attached to the interior surface of the chassis or the absorbent assembly in the crotch region for the same purpose. For example, in the embodiment shown in FIG. 1 and FIG. 2, the upper walls 54 of the lowermost containment pockets 50a and 50b are attached to the inner liner 22 of the chassis 100 in the respective lowermost pocket attachment zones 109a and 109b.

The lowermost pocket attachment zones 109a and 109b may be disposed symmetrically with respect to either or both of the longitudinal axis 42 and the lateral axis 44. Alternatively, the lowermost pocket attachment zones 109a and 109b may be disposed asymmetrically with respect to either or both of the longitudinal axis 42 and the lateral axis 44. For example, the lowermost pocket attachment zones 109a and 109b shown in FIG. 1 are disposed symmetrically with respect to the longitudinal axis 42 and asymmetrically with respect to the lateral axis 44. In particular, the lowermost pocket attachment zones 109a and 109b shown in FIG. 1 are disposed asymmetrically toward the front waist region 36.

Alternatively or in addition, the upper and lower walls of each of the layered containment pockets lying above the lowermost containment pockets may be attached together in the crotch region in such a way as to prevent their unfoldment when lateral tension is applied. For example, in the embodiment shown in FIG. 1 and FIG. 2, the upper walls 54 of the overlying containment pockets 50c and 50d are attached to the respective lower walls 55 in the pocket wall attachment zones 59. The pocket wall attachment zones 59 may be disposed either symmetrically or asymmetrically with respect to either or both of the longitudinal axis 42 and the lateral axis 44, similarly to the alternative dispositions of the lowermost pocket attachment zones 109a and 109b.

Within the extent of the lowermost pocket attachment zones 109a and 109b and the pocket wall attachment zones 59, the attachment pattern may be continuous or intermittent. For example, a film of an adhesive may be applied continuously over the entire area of the attachment pattern and then used to continuously attach the upper wall of a containment pocket. As another example, an adhesive may be applied discontinuously at and inside the boundaries of an attachment pattern, such as in the form of dots, stripes, beads, spirals, etc., and then used to attach the upper wall. Similarly, as another example, an attachment pattern may contain multiple discrete bonds formed by heat sealing, ultrasonic sealing, etc.

Adjacent to the front and back waist edges 136 and 138 of the chassis 100, the overlapped layered containment pockets may remain unattached to the interior surface of the chassis and/or to each other and so remain free to unfold under lateral tension. Thus, in an embodiment in which the layered containment pockets are attached in the crotch region in such a way as to prevent their unfoldment but remain free to unfold in the waist regions, the application of opposing lateral tensile forces to the distal edges 158 of the side flaps 147 to prepare the disposable diaper for use and/or as the disposable diaper is applied and while it is worn causes the side edges 137 to curve concavely and the waist edges 136 and 138 to curve convexly as shown in FIG. 1. The result of this curving of the edges is the distinctive "bowtie" shape (alternatively called a "butterfly" shape) of the chassis 100 shown in this figure. This shape may help to conform the diaper 20 to the contour of the wearer's body in use. Such a shape may also be desirable in order to impart a tailored appearance to the diaper 20 when it is worn and/or to impart an impression that the diaper 20 will fit comfortably between the legs of a wearer.

As shown in FIG. 1, FIG. 2, and FIG. 3, the exemplary chassis 100 also has longitudinally extending and laterally opposing left and right side flaps 147a and 147b that are disposed on the interior portion of the diaper 20 that faces inwardly toward the wearer and contacts the wearer. The side flaps are formed by folding portions of the chassis 100 lying between the respective uppermost layered containment pockets 50c and 50d and the respective left outer side edge 155a and right outer side edge 155b laterally outward, i.e., away from the longitudinal axis 42, to form the respective side flaps 147a and 147b. Each side flap 147 has a proximal edge 157 that is formed by the upper edge 53 of the respective uppermost layered containment pocket. Each side flap also has a distal edge 158 that is formed by the respective original outer side edge 155 of the chassis in its pre-folded condition.

Whatever laterally opposing portions of the chassis extend laterally distally relative to all other portions of the chassis form the side edges 137 of the chassis. Thus, when the distal edge 158 of a side flap 147 extends laterally beyond all of the apices 51 of the respective underlying containment pockets 50, as in FIG. 2, the distal edge 158 forms the respective side edge 137 of the chassis. Alternatively, an apex of one of the containment pockets may extend laterally beyond the distal edge of the side flap and thereby form the side edge of the chassis.

Each side flap 147 preferably includes a longitudinally extensible flap elastic member that is attached adjacent to the distal edge 158 of the side flap by any of many well-known means. Each such flap elastic member may be attached over its entire length or over only a portion of its length. For example, such a flap elastic member may be attached only at or near its longitudinally opposing ends and may be unattached at the middle of its length. Such a flap elastic member may be disposed in the crotch region 37 and may extend into one or both of the front waist region 36 and the back waist region 38. For example, in the exemplary chassis 100 shown in FIG. 1, an elastic strand 167a is attached adjacent to the distal edge 158a of the left side flap 147a and extends into both the front waist region 36 and the back waist region 38. Similarly, an elastic strand 167b is attached adjacent to the distal edge 158b of the right side flap 147b and extends into both the front waist region 36 and the back waist region 38.

Each flap elastic member may be enclosed inside a folded hem. For example, in the exemplary chassis 100 shown in FIG. 2, FIG. 7, and FIG. 9, the elastic strand 167a is enclosed inside a hem 170a formed adjacent to the distal edge 158a of the left side flap 147a and the elastic strand 167b is enclosed inside a hem 170b formed adjacent to the distal edge 158b of the right side flap 147b. Alternatively, the flap elastic member may be sandwiched between two layers of the chassis, e.g., between the layers of a laminate backsheet or between a backsheet and an inner liner. As another alternative, the flap elastic member may be attached on a surface of the chassis 100 and remain exposed.

When stretched, the flap elastic member allows the adjacent side flap distal edge 158 to extend as shown in FIG. 1. When allowed to relax, the flap elastic member contracts and gathers the side flap distal edge 158. The contractive forces of the elastic strands 167a and 167b pull the front waist region 36 and the back waist region 38 toward each other and thereby bend the diaper 20 into a "U" shape in which the interior of the "U" shape is formed by the portions of the diaper 20 that are intended to be placed toward the body of the wearer. Because the distal edges 158 remain free, the contractive forces of the elastic strands 167 lift the distal edges 158 away from the interior surface 102 of the chassis 100. This lifting of the distal edges 158 when the diaper 20 is in the relaxed condition lifts the side flaps 147 into position to serve as side barriers adjacent to the side edges 237 of the absorbent assembly 200.

When the diaper 20 is worn, the relaxed "U" shape generally conforms to the body of the wearer such that the front waist region 36 and the back waist region 38 can be fastened together to encircle the waist and the legs of the wearer. When the diaper 20 is worn in this manner, the elastic strands 167 tend to hold the lifted distal edges 158 of the side flaps 147 in contact with the body of the wearer and thereby form seals to help prevent the leakage of deposited bodily waste out of the diaper 20.

A portion or the whole of the chassis 100 may be made extensible to a degree greater than the inherent extensibility of the material or materials from which the chassis is made, e.g., the backsheet 26, the inner liner 22, or both. The additional extensibility may be desirable in order to allow the chassis 100 to conform to the body of a wearer during movement by the wearer and/or to allow the user to extend the front waist region 36, the back waist region 38, or both waist regions of the chassis 100 to encircle the waist of an individual wearer whose waist circumference falls within a predefined range, i.e., to tailor the diaper to the individual wearer. In addition, the additional extensibility may be desirable in order to minimize the cost of the diaper. For example, an amount of material that would otherwise be sufficient only to make a relatively smaller diaper lacking this extensibility can be used to make a diaper capable of being extended to fit a wearer larger than the smaller diaper would fit. In other words, a lesser amount of material is needed in order to make a diaper capable of being properly fit onto a given size of a wearer when the material is made extensible as described. The portion of the chassis in one of the waist regions may be made laterally extensible to a maximum extensibility greater than a maximum extensibility of another portion of the chassis in the crotch region such that a lateral extension of each of the portions to its maximum extensibility imparts an hourglass shape to the chassis.

Figure 10:
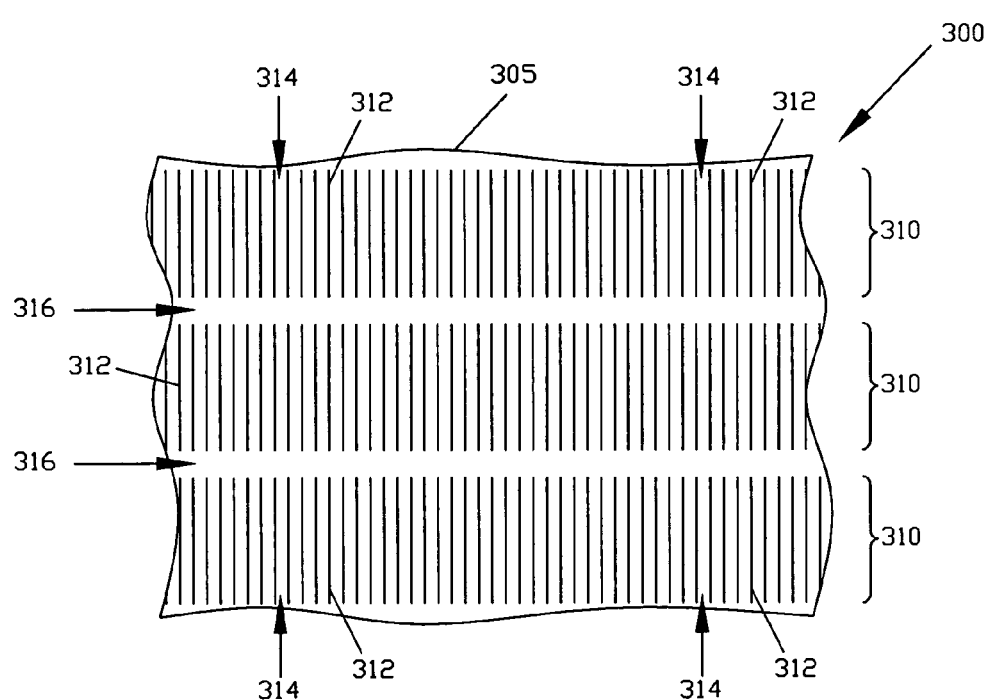
FIG. 10 is a plan view of an exemplary fragment 300 of a formed web material.

Additional lateral extensibility in the chassis 100 may be provided in a variety of ways. For example, a material or materials from which the chassis 100 is made may be pleated by any of many known methods. Alternatively, all or a portion of the chassis may be made of a formed web material or a formed laminate of web materials like those described in U.S. Pat. No. 5,518,801 issued on 21 May 1996 in the name of Chappell et al. An exemplary fragment 300 of such a formed web material 305 is shown in FIG. 10. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

The front waist region 36 and the back waist region 38 can be fastened together to encircle the waist and the legs of the wearer in many well-known ways. For example, separate fastening devices such as safety pins, separate tapes, a separate tie strap or straps, and/or a separate belt can be used for this purpose. Alternatively or in addition, fastening elements can be incorporated into the chassis 100 to enable a user to apply the diaper 20 to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. These incorporated fastening elements may project laterally outward, i.e., away from the longitudinal axis 42 beyond one or both of the side edges 137a and 137b and/or may project longitudinally outward, i.e., away from the lateral axis 44 beyond one or both of the waist edges 136 and 138 or they may lie entirely inside the edges of the diaper 20. When a laminate backsheet is used and is oriented with the nonwoven disposed exteriorly, some forms of mechanical fasteners that typically require specific mating fastener elements, such as hooks that mate with loops, may be configured to engage with the nonwoven and thereby make the inclusion of the specific mating fastener element unnecessary.

For example, laterally opposing adhesive tape tabs may be attached to the chassis 100 at or adjacent to the side edges 137a and 137b of the diaper 20. In use, the adhesive tape tabs may be adhered to the exterior surface 104 of the chassis 100 in the front waist region 36 to fasten the back waist region 38 to the front waist region 36 in a back-over-front manner. Alternatively, similar adhesive tape tabs may be attached to the chassis 100 in the front waist region 36 and used to fasten the front waist region 36 to the back waist region 38 in a front-over-back manner. Suitable adhesive tapes are available from the 3M Corporation of St. Paul, Minn., U.S.A., under the designation of XMF99121. Suitable configurations of adhesive tape tabs are shown in U.S. patent application Ser. No. 10/770,043 filed on 2 Feb. 2004.

Optionally, one or more fastening sheets may be attached onto the exterior surface 104 of the chassis 100. When a fastening sheet is provided, the adhesive tape tabs may be adhered to the fastening sheet to fasten the back waist region 38 and the front waist region 36 together. The fastening sheet may be formed of a material used elsewhere in the diaper, such as a film or a nonwoven. The fastening sheet serves to distribute the tensile force transmitted by each of the adhesive tape tabs over an area of the backsheet 26 that is larger than the adhered area of the adhesive tape tab. In addition, when a single contiguous fastening sheet is used, the fastening sheet may, itself, bear a portion of the tensile force between the laterally opposing adhesive tape tabs and thereby relieve a portion of the force exerted on the backsheet. Thus, the incorporation of such a fastening sheet may be desirable, for example, in order to make it possible to use a relatively inexpensive and relatively weak material for the backsheet 26. Therefore, the total cost of a diaper having a fastening sheet may be less than the total cost of a diaper having a backsheet having sufficient strength for adhesive tape tabs to be adhered directly to the exterior surface of the backsheet.

As another example, cohesive fastening elements may be used. Exemplary fastening elements in the form of cohesive fastening patches may be formed of an inherently crystalline water-based synthetic elastomer to which a tackifying agent has been added to disrupt the polycrystalline structure and thereby render the elastomer cohesive. Such synthetic cohesive products are available from Andover Coated Products, Incorporated, of Salisbury, Mass., U.S.A. and are described in U.S. Pat. No. 6,156,424 issued on 5 Dec. 2000 in the name of Taylor. Cohesive fastening patches may be disposed on the exterior and/or interior surfaces of the chassis in arrangements that allow exclusively for either back-over-front fastening or front-over-back fastening of the waist regions together. Alternatively, the cohesive fastening patches may be disposed in a reversible configuration that is adapted to provide the user of the diaper with both options for fastening, i.e., either back-over-front or front-over-back, in the same diaper, according to personal preference. Suitable configurations of cohesive fastening elements are shown in U.S. patent application Ser. No. 10/770,043 filed on 2 Feb. 2004.

Description of the Absorbent Assembly

The absorbent assembly 200 may be attached to the chassis 100 over any part or the whole of the area of the absorbent assembly 200.

The absorbent assembly 200 may have a planar configuration, i.e., it may be generally flat and unfolded. However, in a preferred configuration, the absorbent assembly is folded along with the chassis to form at least the lowermost layered containment pockets. For example, in the embodiment shown in FIG. 2, the absorbent assembly is folded with the chassis and extends into both the upper walls 54 of the lowermost containment pockets 50a and 50b and the lower walls 55 of the containment pockets 50c and 50d overlying the lowermost pockets.

Figure 11:
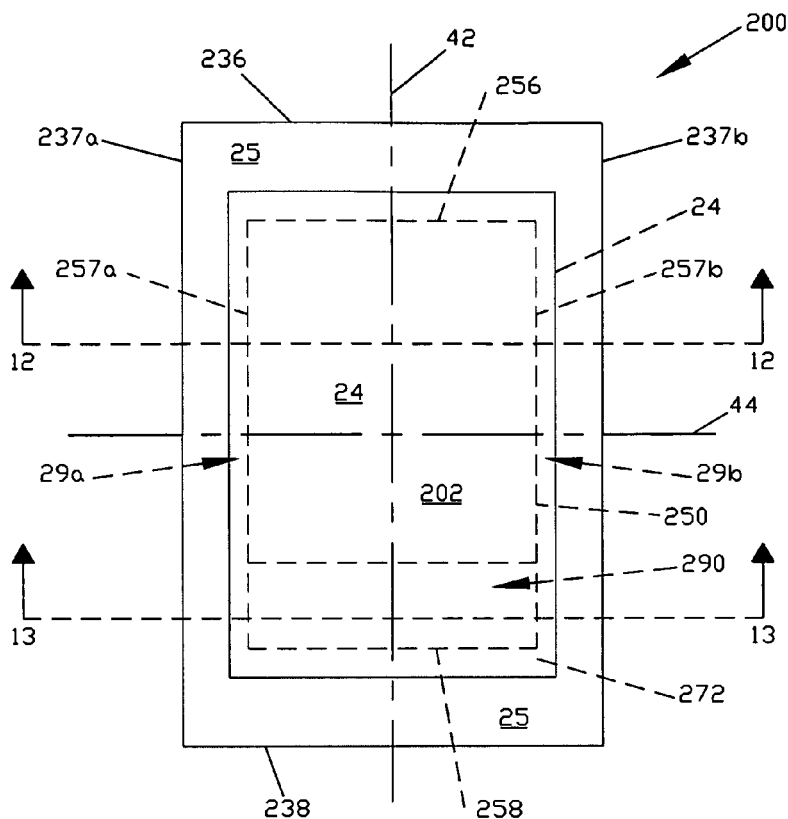
FIG. 11 is a plan view of an exemplary absorbent assembly 200.
Figure 12:
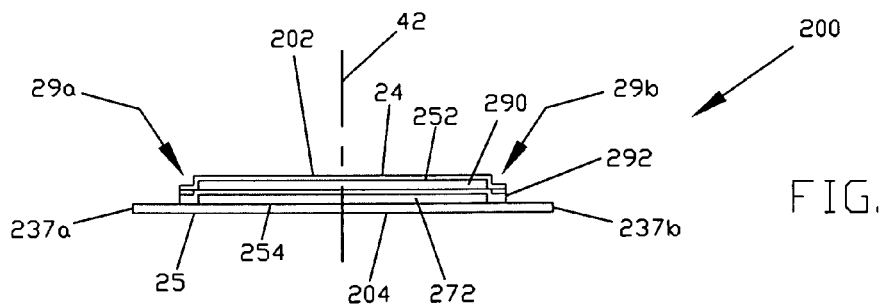
FIG. 12 is a section view of the absorbent assembly 200 of FIG. 11 taken at the section line 12-12.
Figure 13:
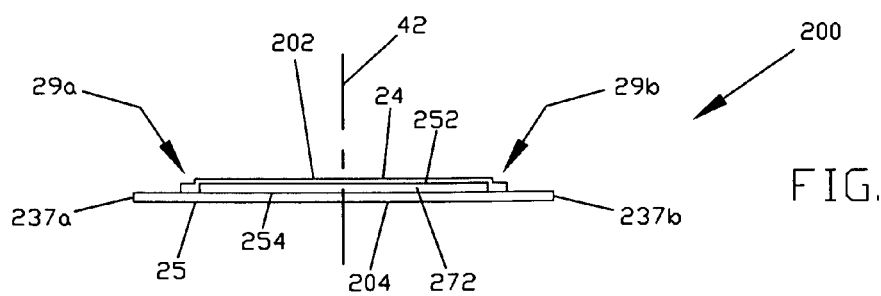
FIG. 13 is a section view of the absorbent assembly 200 of FIG. 11 taken at the section line 13-13.

As shown in FIG. 11, FIG. 12, and FIG. 13, the absorbent assembly 200 includes an absorbent core 250 that serves to absorb and retain liquid bodily waste materials. The absorbent core 250 has a laterally extending front edge 256 and a longitudinally opposing and laterally extending back edge 258. The absorbent core 250 also has a longitudinally extending left side edge 257a and a laterally opposing and longitudinally extending right side edge 257b, both absorbent core side edges extending longitudinally between the front edge 256 and the back edge 258. The absorbent core 250 also has an interior surface 252 and an exterior surface 254.

The absorbent core 250 may be disposed between a lower covering sheet that is disposed on the exterior face of the absorbent core 250 and an upper covering sheet that is disposed on the interior face of the absorbent core 250. Such an upper covering sheet and lower covering sheet may be attached together to contain the absorbent core 250 between them and thereby form the absorbent assembly 200. For example, in the exemplary absorbent assembly 200 shown in FIG. 11, FIG. 12, and FIG. 13, an upper covering sheet 24 and a lower covering sheet 25 are attached together at or adjacent to the side edges 237a and 237b of the absorbent assembly 200 in longitudinally extending adhesive attachment zones 29a and 29b. Alternatively, the upper covering sheet 24 and the lower covering sheet 25 may be attached together in places other than the side edges 237a and 237b of the absorbent assembly 200, e.g., at or adjacent to the end edges 236 and 238 of the absorbent assembly 200, or at or adjacent to both the end edges 236 and 238 and the side edges 237a and 237b.

The upper covering sheet 24 is water-permeable and allows liquid waste to pass through to the absorbent core 250, where the liquid waste is absorbed. The lower covering sheet 25 may be water-impermeable. However, the lower covering sheet 25 preferably is water-permeable. In embodiments in which both the upper covering sheet 24 and the lower covering sheet 25 are water-permeable, any liquid waste that is deposited onto the upper covering sheet 24 but does not pass through the upper covering sheet 24 to the absorbent core 250 can flow around an edge of the absorbent assembly 200 to reach the lower covering sheet 25 and then pass through the lower covering sheet 25 to the absorbent core 250.

The upper covering sheet 24 may form the interior surface 202 of the absorbent assembly 200 that is intended to be placed against the body of the wearer. The upper covering sheet 24 preferably is formed of a soft material that will not irritate the skin of the wearer. Many materials that are suitable for a water-permeable covering sheet are well-known in the art, including synthetic nonwovens such as spunbonded or carded polypropylene, polyester, or rayon. Likewise, many materials that are suitable for a covering sheet that is water-impermeable are well-known in the art, including the materials that are suitable for the backsheet 26.

The upper covering sheet 24 and the lower covering sheet 25 may extend to the same width and the same length. For example, both the upper covering sheet 24 and the lower covering sheet 25 may extend to the front edge 236 and back edge 238, as well as to the left side edge 237a and right side edge 237b of the absorbent assembly 200.

Alternatively, the upper covering sheet 24 and the lower covering sheet 25 may differ in size. For example, in the exemplary absorbent assembly 200 shown in FIG. 11, FIG. 12, and FIG. 13, the upper covering sheet 24 extends longitudinally only to a slightly greater extent than is necessary to cover the absorbent core 250, while the lower covering sheet 25 extends longitudinally beyond the upper covering sheet 24 to the front and back edges 236 and 238 of the absorbent assembly 200. Such an extended covering sheet may serve to isolate the skin of the wearer from a portion of the backsheet 26 as may be desirable, for example, when the diaper 20 is worn under conditions in which contact between the skin and a backsheet film could be uncomfortable.

As another example, the lower covering sheet 25 may be larger than the upper covering sheet 24 and may be wrapped over the side edges 257a and 257b of the absorbent core 250 onto the interior surface of the absorbent core 250, where the upper covering sheet 24 and the lower covering sheet 25 may be attached together.

Alternatively, in place of a separate upper covering sheet 24 and a separate lower covering sheet 25, a single covering sheet may be wrapped around the absorbent core 250 and attached to itself to contain the absorbent core 250. Such a single covering sheet forms an upper layer and a lower layer when wrapped around the absorbent core 250 and, in general, the description of the separate upper covering sheet 24 and lower covering sheet 25 are intended to apply to such upper and lower layers of a wrapped single covering sheet.

The absorbent core 250 includes a storage component 272 that serves to absorb and retain liquid bodily waste materials. Suitable known materials for the absorbent core storage component include cellulose fibers in the form of comminuted wood pulp, commonly known as "airfelt", natural or synthetic fibrous materials, and superabsorbent polymers, used either singly or in mixtures and commonly formed into layers or sheets, etc. These absorbent materials may be used separately or in combination. Many known absorbent materials may be used in a discrete form, i.e., in the form of fibers, granules, particles, and the like. Such a discrete form of an absorbent material may be immobilized by an adhesive that attaches the discrete pieces together to form a coherent layer or that attaches the discrete pieces to a substrate layer or that attaches the discrete pieces both to each other and to the substrate layer.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. For example, the acquisition component may be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materials are more fully described in U.S. Pat. No. 4,950,264 issued to Osborn on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Such an absorbent core acquisition component 290 is shown overlying the absorbent core storage component 272 in FIG. 11, FIG. 12, and FIG. 13. A separation sheet 292 of, e.g., a tissue or a nonwoven material, may be disposed between the absorbent core storage component 272 and the absorbent core acquisition component 290 to help ensure that none of the gel formed by a superabsorbent polymer that may be included in the absorbent core storage component reaches the skin of the wearer. This separation sheet 292 may extend laterally beyond the side edges 257a and 257b of the absorbent core 250 and the upper covering sheet 24 may be attached to the separation sheet 292. In this arrangement, the liquid bodily waste material that is deposited onto the upper covering sheet 24 will pass through the thickness of the upper covering sheet 24 to be absorbed by the absorbent core acquisition component 290, and some or all of it may then pass through the thickness of the separation sheet 292 and then be absorbed and retained by the absorbent core storage component 272.

Figure 14:
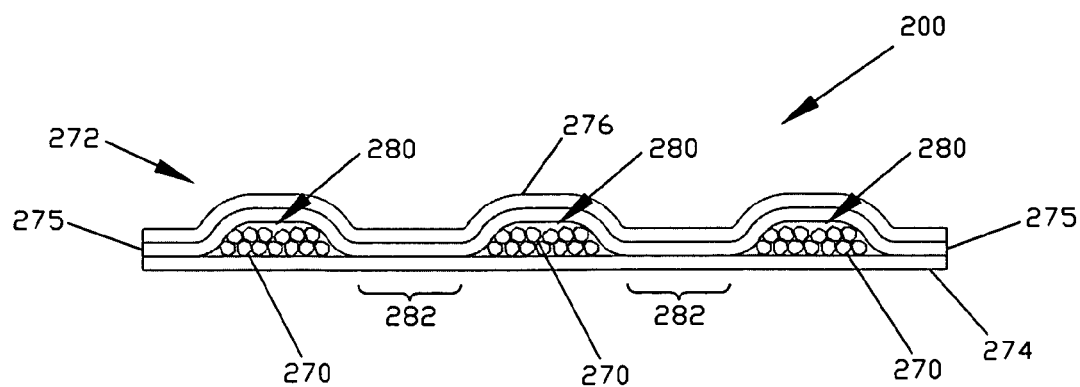
FIG. 14 is a section view of an exemplary absorbent assembly 200 showing details of an exemplary absorbent core.

In some exemplary embodiments, an absorbent core storage component may include the discrete form of an absorbent material that is immobilized in pockets formed by a layer of a thermoplastic material, such as a hot melt adhesive, that intermittently contacts and adheres to a substrate sheet, while diverging away from the substrate sheet at the pockets. Absorbent core components having such structures and being suitable for the storage of liquid bodily wastes are described in co-pending and commonly assigned U.S. patent applications Ser. Nos. 10/776,839 and 10/776,851, both filed on 11 Feb. 2004 in the name of Ehrnsperger et al. An exemplary absorbent core storage component 272 having such a structure is shown in FIG. 14. In this absorbent core storage component 272, particles 270 of a superabsorbent polymer are contained inside pockets 280 formed by a layer 275 of a thermoplastic material. The absorbent core storage component may include both particles of a superabsorbent polymer and airfelt and both materials may be contained inside the pockets formed by the layer of the thermoplastic material. Alternatively, as shown in FIG. 14, an exemplary absorbent core storage component may contain no airfelt and therefore the component can be made relatively thinner and more flexible for the comfort of the wearer. In addition, the particles of the superabsorbent polymer can be immobilized relatively more easily in the absence of airfelt. As shown in FIG. 14, the layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 may have the form of a sheet of fibers of the thermoplastic material through which the liquid bodily waste may pass to be absorbed by the particles 270 of the superabsorbent polymer.

In FIG. 14, a separate thermoplastic layer covering sheet 276 is shown overlying the layer 275 of the thermoplastic material. Alternatively, the separate thermoplastic layer covering sheet 276 may be omitted. As another alternative, two absorbent core storage components each like that shown in FIG. 14 except for the omission of the thermoplastic layer covering sheet 276 may be superposed with one absorbent core storage component inverted such that the respective substrate sheets distally oppose each other. In such a combination of absorbent core storage components, either or both of the distally opposing substrate sheets may serve respectively as either or both of an upper covering sheet and a lower covering sheet for the absorbent assembly. Alternatively, the absorbent assembly may include a separate lower covering sheet and/or a separate upper covering sheet.

STATEMENTS OF INCORPORATION BY REFERENCE AND INTENDED SCOPE OF CLAIMS

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable diaper comprising:
    an absorbent assembly comprising an absorbent core;
    a chassis having a longitudinal axis, a lateral axis, a front waist region having a front waist edge, a back waist region having a back waist edge, a crotch region between the waist regions, laterally opposing side edges extending between the front waist edge and the back waist edge, and an interior surface, the chassis forming a waist opening and two laterally opposing leg openings when the front waist region and the back waist region are attached together,
    the chassis comprising a water-impermeable backsheet and laterally opposing layered containment pockets including on each side of the longitudinal axis a lowermost containment pocket and at least one overlying containment pocket layered interiorly of the lowermost containment pocket, each containment pocket having a closed apex formed by folding a portion of the chassis laterally inward, laterally inwardly facing open side having an upper edge disposed proximally relative to the apex, an upper wall connecting the apex and the upper edge, a lower wall, and a depth defined by the upper edge and the apex;

a portion of the chassis folded laterally outward to form laterally outwardly extending side flaps disposed interiorly of the layered containment pockets;

wherein the absorbent assembly is disposed at least partially laterally between the lowermost containment pockets;

wherein a distal edge of each of the side flaps extends laterally distally beyond the apices of the respective layered containment pockets and thereby forms a respective one of the side edges of the chassis; and wherein the depth of the at least one overlying containment pocket is different from the depth of the at least one lowermost containment pocket.

2. The disposable diaper of claim 1 wherein the absorbent assembly extends into the upper wall of the lowermost containment pocket.

3. The disposable diaper of claim 1 wherein the absorbent assembly extends into both the upper wall of the lowermost containment pocket and the lower wall of the overlying containment pocket.

4. The disposable diaper of claim 1 wherein the proximal upper edge of the overlying containment pocket is disposed laterally equidistantly to the proximal upper edge of the lowermost containment pocket.

5. The disposable diaper of claim 1 wherein the proximal upper edge of the overlying containment pocket is disposed laterally distally relative to the proximal upper edge of the lowermost containment pocket.

6. The disposable diaper of claim 1 wherein the upper wall of the lowermost containment pocket is attached to the interior surface of the chassis in the crotch region in such a way as to prevent unfoldment of the lowermost containment pocket.

7. The disposable diaper of claim 6 wherein the upper wall and the lower wall of the overlying containment pocket are attached together in the crotch region in such a way as to prevent unfoldment of the overlying containment pocket.

8. The disposable diaper of claim 6 having a shape wherein the waist edges are convexly curved and the side edges are concavely curved such that the chassis has a bowtie shape.

9. The disposable diaper of claim 1 wherein each of the side flaps includes a longitudinally extensible flap elastic member attached adjacent to a distal edge of the side flap.

10. The disposable diaper of claim 1 wherein the backsheet comprises a laminate of a nonwoven and a film.

11. The disposable diaper of claim 1 wherein the backsheet is water vapor-permeable.

* * * * *